United States Patent
Stukan et al.

(10) Patent No.: US 10,613,251 B2
(45) Date of Patent: Apr. 7, 2020

(54) METHOD FOR PREDICTION OF LIVE OIL INTERFACIAL TENSION AT RESERVOIR CONDITIONS FROM DEAD OIL MEASUREMENTS

(71) Applicant: SCHLUMBERGER TECHNOLOGY CORPORATION, Sugar Land, TX (US)

(72) Inventors: Mikhail Stukan, Moscow (RU); Bastian Sauerer, Dhahran (SA); Wael Abdallah, Al-Khobar (SA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 375 days.

(21) Appl. No.: 15/367,635

(22) Filed: Dec. 2, 2016

(65) Prior Publication Data
US 2018/0156939 A1    Jun. 7, 2018

(51) Int. Cl.
*G01V 99/00*    (2009.01)
*G01N 33/28*    (2006.01)
(Continued)

(52) U.S. Cl.
CPC ............ *G01V 99/005* (2013.01); *E21B 47/06* (2013.01); *E21B 47/065* (2013.01);
(Continued)

(58) Field of Classification Search
CPC ....... G01V 99/005; G06F 17/50; G06F 17/11; G01N 33/28; G01N 9/36;
(Continued)

(56) References Cited

U.S. PATENT DOCUMENTS

2008/0173076 A1    7/2008  Robin
2008/0236845 A1   10/2008  Morrow et al.
(Continued)

OTHER PUBLICATIONS

"Sampling Petroleum Reservoir Fluids" API Recommended Practice 44: API Petroleum Institute [retrieved on Dec. 27, 2018]. Retrieved from <http://www.ipt.ntnu.no/~curtis/courses/PhD-PVT/PVT-HOT-Vienna-May-2016x/presentations-and-papers/API-RP-44-Sampling-2nd-ed.pdf> (Year: 2003).*
(Continued)

*Primary Examiner* — Rehana Perveen
*Assistant Examiner* — Alfred H B Wechselberger

(57) ABSTRACT

Methods may include measuring an interfacial tension (IFT) for a dead oil sample prepared from a fluid within an interval of a formation; calculating a gas:oil ratio for the fluid within the interval of a formation at a specified temperature and pressure; calculating a live oil density for the fluid within the interval of a formation for the specified temperature and pressure; and converting the IFT for the dead oil sample to a corrected IFT measurement for a live oil within the interval of the formation from the calculated gas:oil ratio and the calculated density. Methods may also include constructing a depletion path for the dead oil sample from one or more isobars and one or more isotherms; and converting the IFT for the dead oil sample to a corrected IFT measurement from the calculated gas:oil ratio and the calculated live oil density for a live oil.

18 Claims, 4 Drawing Sheets

(51) Int. Cl.
    *E21B 47/06*   (2012.01)
    *E21B 49/08*   (2006.01)
    *G01N 9/36*    (2006.01)
    *G01N 13/02*   (2006.01)
    *G06F 17/11*   (2006.01)
    *G06F 17/50*   (2006.01)

(52) U.S. Cl.
    CPC ............ *E21B 49/087* (2013.01); *G01N 9/36* (2013.01); *G01N 13/02* (2013.01); *G01N 33/2823* (2013.01); *G06F 17/11* (2013.01); *E21B 49/088* (2013.01); *E21B 2049/085* (2013.01); *G01N 2013/0283* (2013.01); *G06F 17/5009* (2013.01)

(58) Field of Classification Search
    CPC ............ G01N 2013/0283; G01N 13/02; E21B 49/087; E21B 47/065; E21B 47/06; E21B 2049/085; E21B 49/088
    See application file for complete search history.

(56) References Cited

U.S. PATENT DOCUMENTS

| | | | |
|---|---|---|---|
| 2009/0125238 A1* | 5/2009 | Barboza | E21B 47/00 702/11 |
| 2011/0042070 A1* | 2/2011 | Hsu | E21B 47/102 166/250.01 |
| 2011/0112815 A1 | 5/2011 | Stukan et al. | |
| 2015/0330962 A1 | 11/2015 | Aquino Olivos et al. | |
| 2016/0024372 A1 | 1/2016 | Najafabadi | |
| 2019/0225870 A1* | 7/2019 | Johns | C09K 8/584 |

OTHER PUBLICATIONS

Ezekwe, N. "Petroleum Reservoir Engineering Practice" Chap 4-5, Prentice Hall: ISBN-13: 978-0-13-715283-4 [retrieved on Dec. 26, 2018]. Retrieved from <http://docshare02.docshare.tips/files/31481/314819498.pdf> (Year: 2011).*

Zuo et al. "Prediction of Interfacial Tensions of Reservoir Crude Oil and Gas Condensate Systems" SPE-38434-PA; doi:10.2118/38434-PA [retrieved on Dec. 13, 2018]. Retrieved from <https://www.onepetro.org/journal-paper/SPE-38434-PA> (Year: 1998).*

"Interfacial tension" PetroWiki [retrieved on Dec. 26, 2018]. Retrieved from <https://web.archive.org/web/20150213032817/https://petrowiki.org/Interfacial_tension> (Year: 2015).*

Nelson, et al. "Phase Relationships in Chemical Flooding" SPE-6773-PA, Society of Petroleum Engineers Journal, vol. 18, Iss. 5 [retrieved on Dec. 26, 2018]. Retrieved from <https://www.onepetro.org/journal-paper/SPE-6773-PA> (Year: 1978).*

Abdul-Majeed et al. "Estimation of gas-oil surface tension" Journal of Petroleum Science and Engineering, vol. 27, pp. 197-200 [retrieved on Dec. 12, 2018]. Retrieved from <https://www.researchgate.net/publication/248254181_Estimation_of_gas-oil_surface_tension> (Year: 2000).*

Freyss et al. "PVT Analysis of Oil Reservoirs" Reservoir Engineering, vol. 37, No. 1, pp. 4-15 [retrieved on Dec. 27, 2018] Retrieved from <https://www.slb.conn/~/media/Files/resources/oilfield_review/ors89/jan89/1_pvt.pdf> (Year: 1989).*

McCain, W. "Reservoir-Fluid Property Correlations—State of the Art" SPE Reservoir Enginering, pp. 262-272 [retrieved on Dec. 28, 2018]. Retrieved from <https://www.onepetro.org/journal-paper/SPE-18571-PA> (Year: 1991).*

Sequeira, D. "Compositional effects on gas-oil interfacial tension and miscibility at reservoir conditions" [thesis] LSU Master's thesis. 4136 [retrieved on 2018—Dec. 2018]. Retrieved from <https://digitalcommons.lsu.edu/gradschool_theses/4136> (Year: 2006).*

Sequeira et al. "Reservoir Condition Measurements of Compositional Effects on Gas-Oil Interfacial Tensions and Miscibility" SPE 113333 pp. 1-24 [retrieved on Jun. 14, 2019]. Retrieved from <https://www.onepetro.org/conference-paper/SPE-113333-MS> (Year: 2008).*

Roshanfekr, M. "Effect of Pressure and Methane on Microemulsion Phase Behavior and Its Impact on Surfactant-Polymer Flood Oil Recovery" [thesis] The University of Texas at Austin [retrieved on Dec. 28, 2018]. Retrieved from <https://repositories.lib.utexas.edu/handle/2152/ETD-UT-2010-12-2548> (Year: 2010).*

Sheng et al. "A Non-equilibrium Model to Calculate Foamy Oil Properties" Journal of Canadian Petroleum Technology, vol. 38, No. 4, pp. 38-45 [retrieved on Dec. 13, 2018]. Retrieved from <https://www.onepetro.org/journal-paper/PETSOC-99-04-04> (Year: 1999).*

Freyss et al. "PVT Analysis for Oil Reservoirs" Oilfield Review, vol. 31, No. 1 [retrieved on Dec. 27, 2018]. Retrieved from <https://www.slb.com/~/media/Files/resources/oilfield_review/ors89/jan89/1_pvt.pdf> (Year: 1989).*

Xu et al. "Measurement of Surfactant-Induced Interfacial Interactions at Reservoir Conditions" SPE Reservoir Evaluation and Engineering, Feb. 2008 pp. 83-94 [retrieved on Jun. 14, 2019]. Retrieved from <https://www.onepetro.org/journal-paper/SPE-96021-PA> (Year: 2008).*

Nobakht et al. "Determination of CO2Minimum Miscibility Pressure from Measured and Predicted Equilibrium Interfacial Tensions" Ind. Eng. Chem. Res. 2008, vol. 47, Iss. 22, pp. 8918-8925 [retrieved on Nov. 12, 2019]. Retrieved from <https://pubs.acs.org/doi/abs/10.1021/ie800358g> (Year: 2008).*

Al-Sahhaf, T., Elkamel, A., Ahmed, A. S. et al. 2005. The Influence of Temperature, Pressure, Salinity, and Surfactant Concentration on the Interfacial Tension of the N-Octane-Water System. Chem. Eng. Comm. 192 (5): 667-684.

Hjelmeland, O. S., Larrondo, L. E. 1986. Experimental Investigation of the Effect of Temperature, Pressure, and Crude Oil Composition on Interfacial Properties. SPE Reservoir Engineering 1 (4):321-328. SPE-12124-PA.

International Search Report and Written Opinion issued in the related PCT Application PCT/US2017/062758, dated Feb. 20, 2018 (15 pages).

International Preliminary Report on Patentability issued in the related PCT Application PCT/US2017/062758, dated Jun. 4, 2019 (11 pages).

* cited by examiner

FIG. 3

302 — Obtain IFT from a dead oil sample from a formation of interest.

304 — Determine the gas:oil ratio for the sample.

306 — Calculate the live oil density for the sample.

308 — Review assembled database to determine an IFT correction factor.

310 — Calculate adjusted IFT for corresponding live oil sample.

METHOD FOR PREDICTION OF LIVE OIL INTERFACIAL TENSION AT RESERVOIR CONDITIONS FROM DEAD OIL MEASUREMENTS

BACKGROUND

The rate of oil recovery from hydrocarbon reservoirs is governed by the interplay of viscous and capillary forces that determine the fluid transport in porous media. Surface active constituents of reservoir fluids may also accumulate at interfaces between fluid phases, such as an oil-brine interface, and phase boundaries between fluids and solids, such as an oil-rock interface, which can change interfacial properties and fluid flow characteristics. Changes at the interphase boundaries also affect the interfacial tension (IFT) and surface wettability. In order to estimate accurately the residual oil saturation and recoverable oil, knowledge of reservoir fluids IFT and reservoir rock wettability is an important factor. The results of IFT measurements depend on temperature, pressure, and fluid composition of a potential hydrocarbon source under reservoir conditions. However, determining IFT under reservoir conditions currently requires isolating and maintaining downhole samples at reservoir conditions, which can increase well down time and overall costs.

SUMMARY

This summary is provided to introduce a selection of concepts that are described further below in the detailed description. This summary is not intended to identify key or essential features of the claimed subject matter, nor is it intended to be used as an aid in limiting the scope of the claimed subject matter.

In one aspect, embodiments of the present disclosure are directed to methods that include measuring an interfacial tension (IFT) for a dead oil sample prepared from a fluid within an interval of a formation; calculating a gas:oil ratio for the fluid within the interval of a formation at a specified temperature and pressure; calculating a live oil density for the fluid within the interval of a formation for the specified temperature and pressure and converting the IFT for the dead oil sample to a corrected IFT measurement for a live oil within the interval of the formation from the calculated gas:oil ratio and the calculated density.

In another aspect, embodiments of the present disclosure are directed to methods that include measuring an interfacial tension (IFT) for a dead oil sample prepared from a fluid within an interval of a formation; calculating a gas:oil ratio for the fluid within the interval of a formation; calculating a live oil density for the fluid within the interval of a formation; constructing a depletion path for the dead oil sample from one or more isobars and one or more isotherms; and converting the IFT for the dead oil sample to a corrected IFT measurement from the calculated gas:oil ratio and the calculated live oil density for a live oil within the interval of the formation.

Other aspects and advantages of the disclosure will be apparent from the following description and the appended claims.

BRIEF DESCRIPTION OF FIGURES

FIG. 3 is a work flow diagram of a method in accordance with an embodiment of the present disclosure.

DETAILED DESCRIPTION

Figure 1:
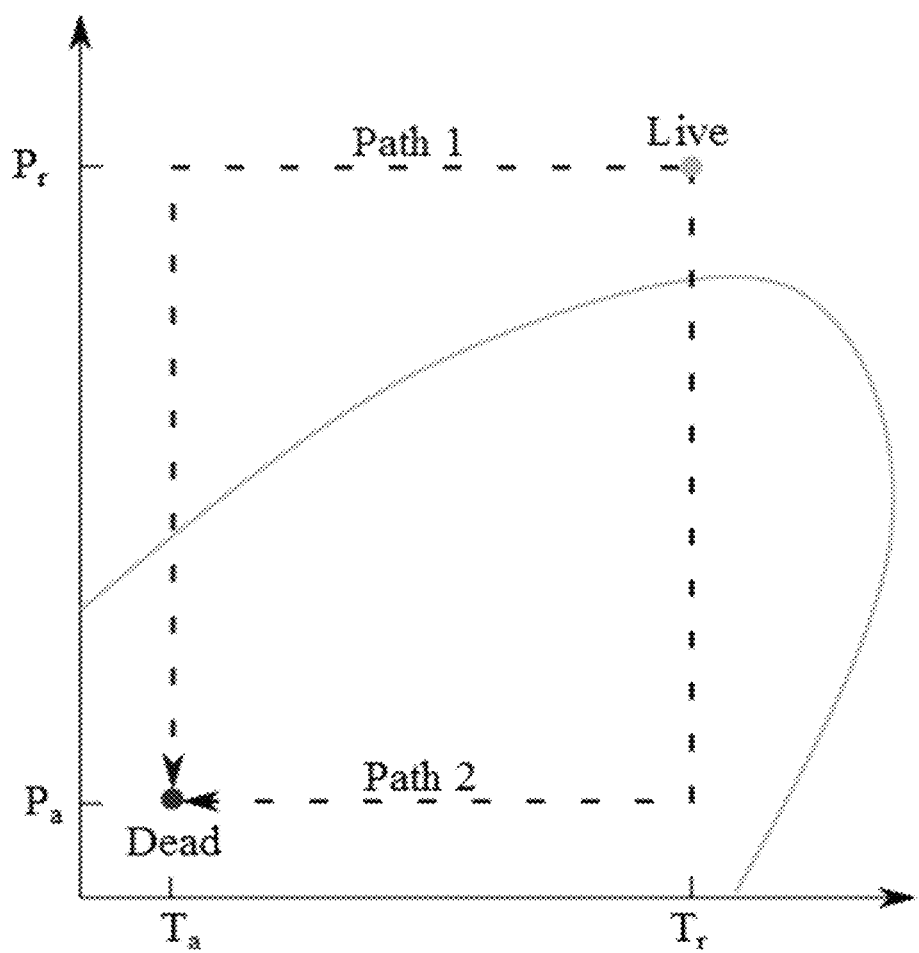
FIG. 1 is a graphical representation depicting a phase diagram of a crude oil sample showing two pathways from live to dead stages in accordance with an embodiment of the present disclosure.

This disclosure relates generally to methods of analyzing formation fluid and gas compositions. In one or more embodiments, data obtained from dead oil IFT measurements and empirical relationships may be used to determine the interfacial tension (IFT) of a hydrocarbon reserve under reservoir conditions. Methods in accordance with the present disclosure may also be used to derive a "correction factor," a set of correction rules that may be used to convert the results of dead oil IFT measurements to a corresponding live oil IFT value. In some embodiments, the correction factor may be used to convert the results of dead oil IFT measurements to an IFT value for the oil at any point along a defined depletion path.

IFT affects the relative permeability of a fluid system within a formation and is a substantial factor in the development of efficient oil recovery protocols and production management. IFT is strongly influenced by temperature, pressure, and oil composition, and it is therefore important to determine the IFT of "live" oil—oil under reservoir conditions. While potentially useful in the design of wellbore operations, live oil IFT is rarely, if ever, used in practice because there are no known techniques to measure the IFT of a live oil downhole, and laboratory measurements require the acquisition of sample downhole and transport to a pressure-volume-temperature (PVT) laboratory under controlled conditions. Sample isolation and transport contribute to added time and material costs, and common practice is often to use the results from "dead" oil—oil under standard temperature and pressure—instead. The use of dead oil measurements may introduce uncertainty because dead oil is often no longer representative of the live oil once collected at the surface, because the oil has undergone significant changes depending on how the sample transitioned from reservoir to surface conditions. Changes in dead oil composition and chemistry that may occur include reductions in gas and volatile content, changes in density, changes in surfactant concentration, and the like, all of which can affect the resulting IFT.

In general, IFT is proportional to the density difference between immiscible fluids in contact, such as oil and water, and reciprocally proportional to interface width, which depends strongly on temperature and surfactant concentration. As the temperature decreases (under isobaric conditions) the IFT is affected by two phenomena. Dissimilarity in the thermal expansion factor for oil and water results in IFT decrease, whereas reduction of thermal smearing of the oil/water boundary causes IFT increase. Based on varying thermodynamic properties for different oils, either of these effects can predominate. Below the saturation pressure, decrease in pressure (under isothermal conditions) corresponds to IFT decrease, because gas release causes an increase of the oil density and surfactant concentration.

In order to address the limitation, methods in accordance with the present disclosure may be used to derive a reconstructed live oil IFT value using measurements performed on dead oil. Reconstructed IFT may be used in a number of planning processes, such as incorporation into a reservoir simulator. For example, IFT is one factor used to describe the moving fluids within the systems, and may be used to estimate oil and water displacement at reservoir temperatures and pressures, including anticipating water cut and the composition of produced fluids. IFT can change over time and/or in neighboring wells, and may be used in some embodiments to predict production quality changes. Moreover, IFT values may be updated during production based on the amount and composition of the output, particularly over time as the levels of hydrocarbon in the reservoir deplete.

In one or more embodiments, methods in accordance the present disclosure may include generating a workflow for reconstruction of live oil interfacial tension (IFT) at reservoir conditions from IFT measurements performed on dead oil samples. In some embodiments, a correction factor may be applied to IFT obtained from dead oil to calculate an IFT for any given set of temperature and pressure values, and for varying oil and chemical compositions. Correction factors may be determined from empirical relationships between dead oil measurements, knowledge of depletion path-dependent compositional changes, and corresponding live oil composition measurements obtained from downhole measurements, such as PVT measurements. In some embodiments, the methods may include developing a database of IFT measurements to populate the thermodynamic pathways from a live oil sample at reservoir conditions to a dead crude oil.

To predict the interfacial tension between crude oil and brine at reservoir conditions based on the results of IFT measurements on dead oil, the transformation the oil passes on the pathway from a live crude oil sample at reservoir conditions to dead crude oil is modeled to estimate the final impact on the IFT value. According to theory, interfacial tension, $\sigma$, between two immiscible fluids that are in contact is directly proportional to the fluid density difference and reciprocally proportional to the interface width according to Eq. 1.

$$\sigma = A \int_{-\infty}^{\infty} \left(\frac{\partial \rho}{\partial z}\right)^2 dz \quad (1)$$

In Eq. 1, A is the mixing energy parameter, z is direction perpendicular to the interface and $\rho$ is defined by Eq. 2, where $\rho_b$ and $\rho_o$ is density of brine and oil respectively, $z_{int}$ the position of the dividing interface, and $\delta$ is the characteristic thickness of the interface.

$$\rho = \frac{\rho_b + \rho_o}{2} + \frac{\rho_b - \rho_o}{2} \mathrm{erf}\left(\frac{z - z_{int}}{\delta}\right) \quad (2)$$

The thickness of the interface $\delta$ depends on temperature and surfactant concentration, while the fluid densities are dependent on temperature, pressure, and fluid composition (the amount of gas dissolved in the fluid).

Taking into account Eq. 2, Eq. 1 can be rewritten as Eq. 3.

$$\sigma = \frac{A}{\delta} \sqrt{\frac{1}{2\pi}} (\rho_b - \rho_o)^2 \quad (3)$$

In one or more embodiments, Eq. 3 may be used to reconstruct IFT at reservoir conditions given fluid phase density, interface thickness, and mixing energy parameter for the fluids.

In one or more embodiments, a correction factor may be obtained to convert a dead oil IFT measurement into an IFT that corresponds to a live oil measurement. In some embodiments, the crude oil thermodynamic pathway may be rationalized as a sequence of isothermal (depressurization at constant temperature) and isobaric (cooling under constant pressure) transformations, and IFT evolution may be quantified with consideration to a number of governing phenomena.

Governing phenomena that contribute to changes in IFT include changes in fluid density associated with the release of gas from a fluid system below saturation pressure, such as in response to a decrease in pressure under isothermal conditions. Further, density changes occur upon the evolution of volatile or "light" components from a fluid system, which also leads to a decrease in the oil-brine density difference and an increase in the surfactant concentration. If the temperature is decreased under isobaric conditions, the IFT is affected by two phenomena having opposing impacts on IFT. On one hand, IFT decreases as the oil-brine density difference decreases, while the IFT increases as the thermal smearing of the oil/brine boundary, associated with the interface thickness $\delta$, is reduced. The overall change in IFT depends in part on crude oil composition and temperature interval, as either factor may govern within different temperature intervals.

With particular respect to FIG. 1, a phase diagram for a crude oil sample is shown with two pathways from live to dead stages. In the simplest case, the "depletion pathway" from live crude to dead crude consists of one isotherm and one isobar shown as Path 1 or Path 2 in FIG. 1. In reality, a "depletion pathway" often does not coincide with either of these paths. When not performed under stringent laboratory control, depressurization is accompanied by temperature decrease, and, similarly, cooling down results in pressure reduction.

Figure 2:
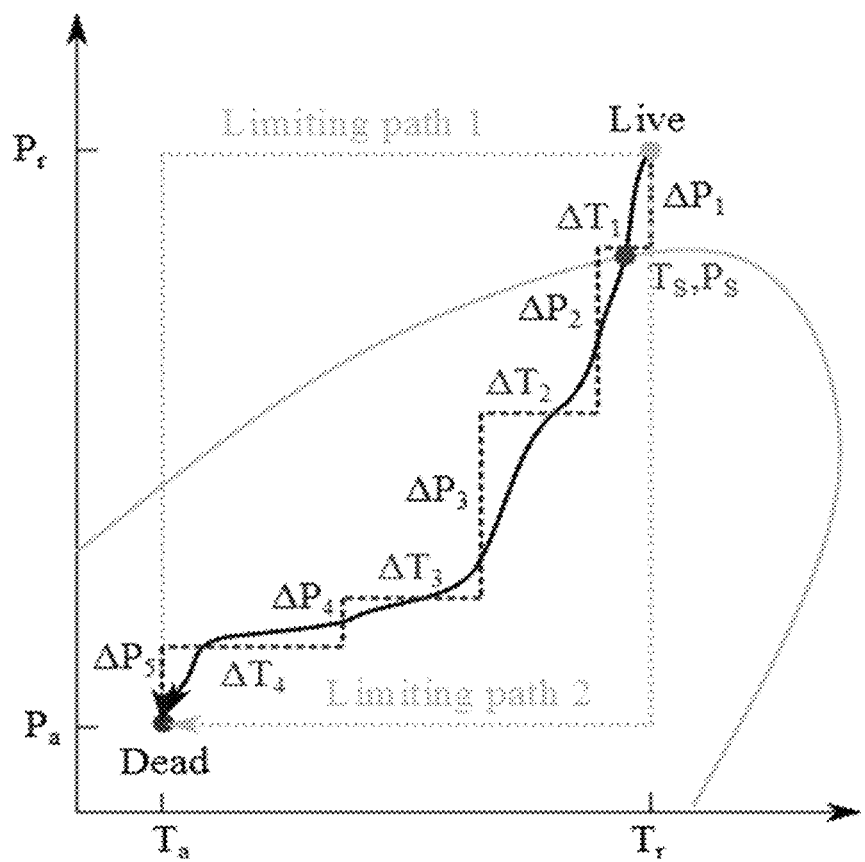
FIG. 2 is a graphical representation depicting a phase diagram of a crude oil sample with a superimposed depletion path in accordance with an embodiment of the present disclosure.

While the actual depletion pathway is usually unknown, sequential coarse graining of isobars and isotherms will result in specific "limiting paths." With particular respect to FIG. 2, a phase diagram showing an example of decomposition of an actual depletion path (solid black line) is shown divided into a sequence of isotherms ($\Delta P_i$) and isobars ($\Delta T_i$) and two limiting paths shown as dashed lines. Limiting path 1 is shown as a single isobar and single isotherm, while limiting path 2 is shown as a single isotherm and single isobar. Within each of the transformation legs, i.e., each isobar or isotherm, IFT dependence on temperature or pressure can be estimated theoretically based on laboratory measurements or experiments on oils with similar properties. IFT dependence within each of these legs is different. Isobars and isotherms are not commutative and depletion/restoration along "Limiting path 1" is not equivalent to depletion/restoration along "Limiting path 2" in FIG. 2.

Deviation of reconstructed IFT from the true IFT value may grow with coarse graining of isobars and isotherms and reaches a maximum for Limiting paths 1 and 2. As the result, restoration of the live oil IFT value along these limiting paths will give the borders of the interval within which the true IFT value is located. In one or more embodiments, the depletion path may also be defined by an operator or by algorithm based on knowledge of formation conditions to improve accuracy. Further, samples of live fluids may be used to determine the IFT along points of a selected depletion path in some embodiments.

In one or more embodiments, methods in accordance with the present disclosure are directed to a workflow, designed to gather information about the thermodynamic dependencies of interfacial tension of a downhole fluid composition at various environmental conditions. With particular respect to FIG. 3, an embodiment of a workflow in accordance with the present disclosure to establish an estimation of live crude oil IFT from dead oil measurements is shown. In some embodiments, methods may begin at 302 by obtaining a sample of dead oil and performing an IFT measurement at standard temperature and pressure.

Next, the ratio of the gas volume leaving the fluid system to the volume of oil at standard conditions, i.e., the gas to oil ratio, gas:oil ratio, or GOR, may be obtained at 304 from measurements obtained downhole to calculate an IFT correction factor. In some embodiments, the IFT correction factor is derived from the estimation of live oil density at reservoir conditions, the interface thickness δ at reservoir conditions, and mixing energy parameter value A. All these parameters are then used in Eq. 3 to get the IFT. The live oil density may be estimated based on GOR by taking into account the amount and composition of gas released from the oil during depletion. Knowing this information and having the compositional analysis of dead oil, it is possible to restore the composition of live oil and calculate its density at reservoir conditions using information from the databases or standard simulation packages, e.g., PVTPRO® commercially available from Schlumberger Technology Corporation. Similar estimates can be performed for δ and A based on the knowledge of IFT dynamics along isotherms and isobars for the given oil or oils with similar composition from a database of known values in some embodiments. Downhole measurements may include the output of a downhole fluid analyzer (DFA), flash analysis (single or multistage) using an onsite separator, or through PVT laboratory analysis using downhole sample. However, other techniques capable of determining the GOR may be used without exceeding the scope of the instant disclosure.

The density for a corresponding live oil sample is then calculated at 306 using known empirical relationships and data obtained from onsite PVT analysis, laboratory analysis or live oil samples, downhole analysis, or using equation of state calculations. However, other techniques capable of determining live oil density may be used without exceeding the scope of the instant disclosure.

Once GOR and live oil density have been calculated, a correction factor may be determined to convert the dead oil measurement to a corresponding live oil measurement. In some embodiments, a correction factor and/or live oil IFT may be established through empirical relationships determined by lab experiments, such as presented in Eq. 3 at 308. In some embodiments, testing for various oil compositions under assorted temperature and pressure conditions, including assays studying possible depletion paths, may be compiled into a database and consulted in a manual or automated process to attain a correction factor for subsequent IFT measurements. Results from the database may be applied to dead oil IFT as a correction factor in some embodiments, or as a correlation based on GOR and density in other embodiments.

An adjusted IFT corresponding to a live oil measurement within the selected interval of a wellbore may then be calculated at 310 using the calculated correction factor. In some embodiments, an IFT correction factor may be obtained to estimate IFT of live oil at reservoir conditions, or at any point along the depletion path at a given pressure and temperature. IFT may be corrected for changes in oil composition and density resulting from, for example, light component and volatiles removal, change in the concentration of various chemical components such as asphaltenes using initial chemical composition determinations from PVT logs. By way of illustration, heavy oils (those having lower API gravity) may have lower capacity to contain dissolved gas than lighter oils, and IFT may vary less over a given temperature and pressure range. Chemical composition gradients may also exist within and between adjacent wells, creating changes in measured IFT.

Figure 4:
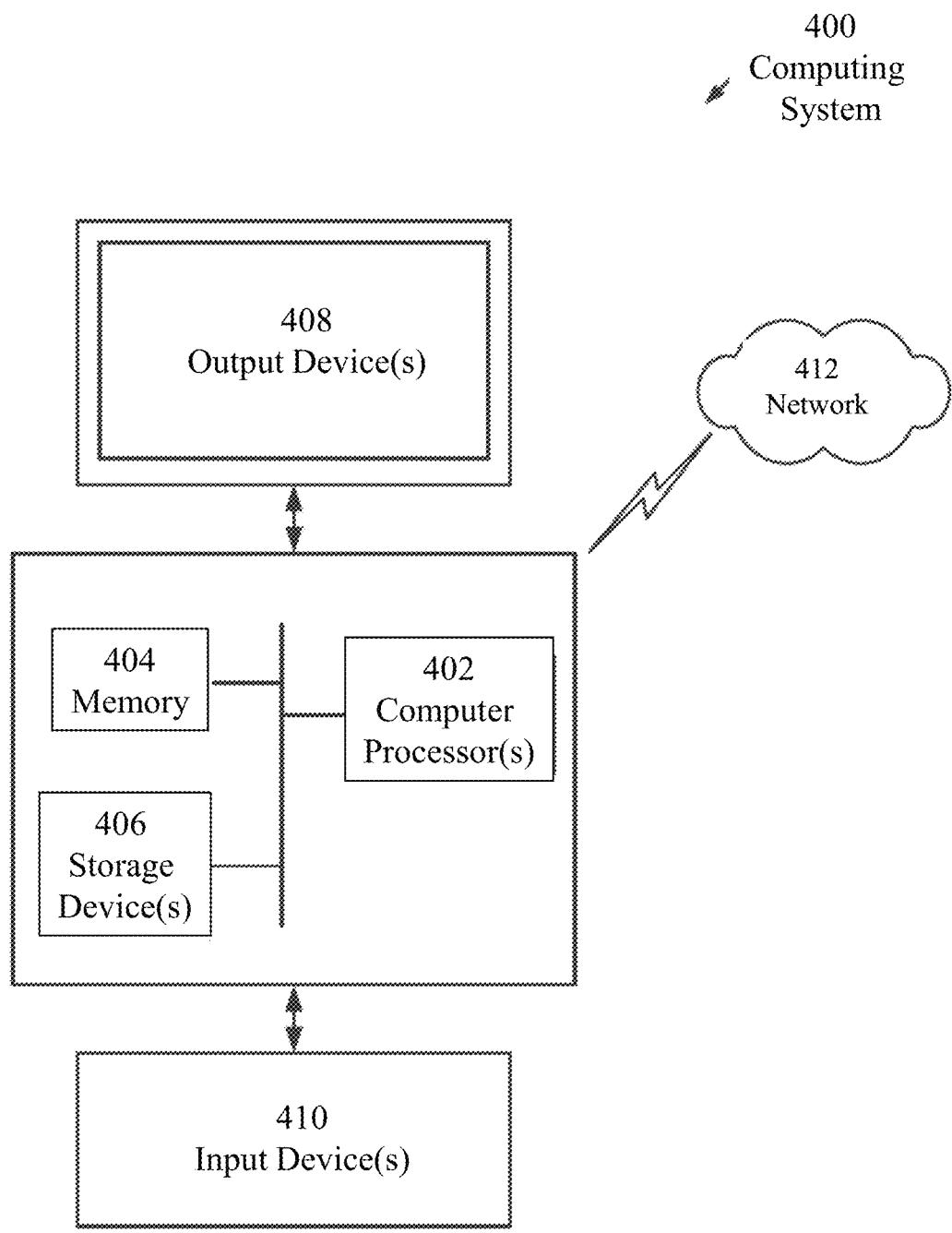
FIG. 4 is a schematic depicting a computer system in accordance with embodiments of the present disclosure.

Embodiments of the present disclosure may be implemented on a computing system. Any combination of mobile, desktop, server, embedded, or other types of hardware may be used. For example, as shown in FIG. 4, the computing system (400) may include one or more computer processor(s) (402), associated memory (404) (e.g., random access memory (RAM), cache memory, flash memory, etc.), one or more storage device(s) (406) (e.g., a hard disk, an optical drive such as a compact disk (CD) drive or digital versatile disk (DVD) drive, a flash memory stick, etc.), and numerous other elements and functionalities. The computer processor(s) (402) may be an integrated circuit for processing instructions. For example, the computer processor(s) may be one or more cores, or micro-cores of a processor. The computing system (400) may also include one or more input device(s) (410), such as a touchscreen, keyboard, mouse, microphone, touchpad, electronic pen, or any other type of input device. Further, the computing system (400) may include one or more output device(s) (408), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (400) may be connected to a network (412) (e.g., a local area network (LAN), a wide area network (WAN) such as the Internet, mobile network, or any other type of network) via a network interface connection (not shown). The input and output device(s) may be locally or remotely (e.g., via the network (412)) connected to the computer processor(s) (402), memory (404), and storage device(s) (406). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments of the invention.

Further, one or more elements of the aforementioned computing system (400) may be located at a remote location and connected to the other elements over a network (412). Further, embodiments of the invention may be implemented on a distributed system having a plurality of nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

Although the preceding description has been described herein with reference to particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed is:

1. A method of predicting live oil interfacial tension at reservoir conditions from dead oil measurements comprising:
   measuring an interfacial tension (IFT) for a dead oil sample prepared from a fluid within an interval of a formation;
   calculating a gas:oil ratio for the fluid within the interval of a formation at a specified temperature and pressure;
   calculating a live oil density for the fluid within the interval of a formation for the specified temperature and pressure;
   converting the IFT for the dead oil sample to a corrected IFT measurement for a live oil within the interval of the formation from the calculated gas:oil ratio and the calculated density; and
   using the corrected IFT measurement in a design of a wellbore operation.

2. The method of claim 1, wherein the corrected IFT is determined at least in part according to the equation:

$$\sigma = \frac{A}{\delta}\sqrt{\frac{1}{2\pi}}(\rho_b - \rho_o)^2$$

where σ is the corrected IFT, A is the mixing energy parameter, δ thickness of the interface, $\rho_b$ is the density of the brine phase in the fluid, and $\rho_o$ is density of the oil phase in the fluid.

3. The method of claim 2, wherein δ and A are estimated based on the knowledge of IFT dynamics along isotherms and isobars derived from a fluid having a similar composition to the fluid within an interval of a formation.

4. The method of claim 1, further comprising developing a reservoir model using the corrected IFT measurement.

5. The method of claim 1, wherein the method comprises calculating the gas:oil ratio, and wherein the gas:oil ratio is determined from one or more from a group consisting of: downhole measurement, wellsite surface measurement, and laboratory measurement.

6. The method of claim 1, wherein the live oil density is determined from a model prediction generated from the components of a live oil.

7. The method of claim 1, wherein the live oil density is determined from laboratory measurements.

8. The method of claim 1, wherein
   the calculating a gas:oil ratio and live oil density is based at least in part on gas:oil ratio and live oil density from a database containing measurements for similar fluid compositions for varying pressure and temperature conditions.

9. The method of claim 1, wherein the specified temperature and pressure corresponds to the temperature and pressure measured within the interval of the formation, and wherein the oil density is a live oil density.

10. A method of predicting live oil interfacial tension at reservoir conditions from dead oil measurements comprising:
    measuring an interfacial tension (IFT) for a dead oil sample prepared from a fluid within an interval of a formation;
    calculating a gas:oil ratio for the fluid within the interval of a formation;
    calculating a live oil density for the fluid within the interval of a formation;
    constructing a depletion path for the dead oil sample from one or more isobars and one or more isotherms;
    converting the IFT for the dead oil sample to a corrected IFT measurement from the calculated gas:oil ratio and the calculated live oil density for a live oil within the interval of the formation; and
    using the corrected IFT measurement in a design of a wellbore operation.

11. The method of claim 10, wherein the corrected IFT is determined according to the equation:

$$\sigma = \frac{A}{\delta}\sqrt{\frac{1}{2\pi}}(\rho_b - \rho_o)^2$$

where σ is the corrected IFT, A is the mixing energy parameter, δ thickness of the interface, $\rho_b$ is the density of the brine phase in the fluid, and $\rho_o$ is density of the oil phase in the fluid.

12. The method of claim 11, wherein δ and A are estimated based on the knowledge of IFT dynamics along isotherms and isobars derived from a fluid having a similar composition to the fluid within an interval of a formation.

13. The method of claim 10, further comprising developing a reservoir model using the corrected IFT measurement.

14. The method of claim 10, wherein the method comprises calculating the gas:oil ratio, and wherein the gas:oil ratio is determined from one or more from a group consisting of downhole measurement, wellsite surface measurement, and laboratory measurement.

15. The method of claim 10, wherein the live oil density is determined from a model prediction generated from the components of a live oil.

16. The method of claim 10, wherein the live oil density is determined from laboratory measurements.

17. The method of claim 10, wherein
    the calculating a gas:oil ratio and live oil density is based at least in part on gas:oil ratio and live oil density from a database containing measurements for similar fluid compositions for varying pressure and temperature conditions.

18. The method of claim 10, wherein the specified temperature and pressure corresponds to the temperature and pressure measured within the interval of the formation, and wherein the oil density is a live oil density.

* * * * *